United States Patent
DiCarlo et al.

(10) Patent No.: US 9,546,977 B1
(45) Date of Patent: Jan. 17, 2017

(54) JUNCTION FIELD EFFECT TRANSISTOR BASED BIOSENSOR

(71) Applicant: INTERNATIONAL BUSINESS MACHINES CORPORATION, Armonk, NY (US)

(72) Inventors: John DiCarlo, Danbury, CT (US); Tak H. Ning, Yorktown Heights, NY (US); Sufi Zafar, Yorktown Heights, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 14/980,798

(22) Filed: Dec. 28, 2015

(51) Int. Cl.
  *G01N 27/416* (2006.01)
  *G01N 27/414* (2006.01)

(52) U.S. Cl.
  CPC ...... *G01N 27/4162* (2013.01); *G01N 27/4167* (2013.01)

(58) Field of Classification Search
  CPC ............ G01N 27/4162; G01N 27/4167; G01N 27/414
  See application file for complete search history.

(56) References Cited

U.S. PATENT DOCUMENTS

| | | | |
|---|---|---|---|
| 4,322,680 A | 3/1982 | Janata et al. | |
| 5,466,348 A | 11/1995 | Holm-Kennedy | |
| 8,114,591 B2 | 2/2012 | Toumazou et al. | |
| 8,728,844 B1* | 5/2014 | Liu | H01L 29/66477 257/252 |
| 8,940,548 B2 | 1/2015 | Khater et al. | |
| 8,999,739 B2 | 4/2015 | Afzali-Ardakani et al. | |
| 9,070,733 B2 | 6/2015 | Rajagopal et al. | |
| 2004/0147969 A1* | 7/2004 | Mann | A61B 5/0215 607/17 |
| 2005/0205891 A1 | 9/2005 | Holm-Kennedy | |
| 2012/0021918 A1* | 1/2012 | Bashir | B82Y 15/00 506/2 |
| 2012/0138460 A1 | 6/2012 | Baghbani-Parizi et al. | |
| 2013/0285026 A1* | 10/2013 | Miskiewicz | H01L 51/0034 257/40 |

(Continued)

OTHER PUBLICATIONS

Crescentini et al.; "Noise Limits of CMOS Current Interfaces for Biosensors: A Review"; IEEE Transactions on Biomedical Circuits and Systems; vol. 8; No. 2; Apr. 2014; pp. 278-292.

(Continued)

*Primary Examiner* — Christine Enad
(74) *Attorney, Agent, or Firm* — Cantor Colburn LLP; Vazken Alexanian

(57) ABSTRACT

In an embodiment of the invention, a biosensor comprises a semiconductor region having a doping polarity; a source region located at a first end of the semiconductor layer and a drain region located at a second end of the semiconductor layer; wherein the source region is in electrical communication with a source voltage; a current path from the source region, through the semiconductor layer, to the drain region; a sensing gate region in contact with a first surface of the semiconductor layer and having an opposite polarity as the semiconductor layer; a sensing surface in electrical communication with the sensing gate region; and a dual gate region in contact with a second surface of the semiconductor layer; wherein the dual gate region has a same polarity as the sensing gate region.

20 Claims, 8 Drawing Sheets

(56) References Cited

U.S. PATENT DOCUMENTS

| | | | | |
|---|---|---|---|---|
| 2015/0044710 A1* | 2/2015 | Dasgupta | ............ | A61B 5/14552 435/8 |
| 2015/0160323 A1* | 6/2015 | Wen | .................... | G01N 27/4145 702/107 |
| 2016/0131613 A1* | 5/2016 | Jayant | ................... | C12Q 1/6869 506/9 |
| 2016/0178569 A1* | 6/2016 | Hoffman | ............ | G01N 27/4145 257/29 |

OTHER PUBLICATIONS

Zafar et al.; "A comparison between bipolar transistor and nanowire field effect transistor biosensors"; Applied Physics Letters vol. 106; No. 6; 2015; 4 pages.

* cited by examiner though the dual gate region is an electrically conducting region; a sensing surface in electrical communication with the sensing gate region; wherein the sensing surface is located on the extended region of the floating gate.

In yet another embodiment of the invention, a method of probing a mixture using a biosensor, the method comprises exposing a sensing surface of the biosensor to the mixture.

JUNCTION FIELD EFFECT TRANSISTOR BASED BIOSENSOR

BACKGROUND

The present invention relates to a dual gate junction field effect transistor based biosensor and methods of making the same.

Biosensors can be used to detect ion concentration (such as pH) or the concentration of biomolecules (such as DNA, miRNA, enzymes, and antibodies) via a detector that can output a signal that can be more easily detected. Examples of output signals include optical signals, physiochemical signals, piezoelectric signals, and electrochemical signals.

Existing biosensors have a number of disadvantages. They are generally bulky, uncomfortable, and poorly suited for long-term use on an outpatient basis, for use with infants, or for use with uncooperative patients, such as patients with dementia who tend to remove existing sensors. Furthermore, many biosensors utilize cumbersome electrodes, for example, requiring clipping electrodes on the fingertips or using adhesive patches. These cumbersome electrodes can severely limit the user's mobility and can result in skin irritation.

An improved biosensor that can easily detect a chemical change or the presence of a biological substance is therefore desired.

SUMMARY

According to an embodiment of the present disclosure relates to a biosensor, a method of making and of using the same.

In an embodiment of the invention, a biosensor comprises a semiconductor region having a doping polarity; a source region located at a first end of the semiconductor layer and a drain region located at a second end of the semiconductor layer; wherein the source region is in electrical communication with a source voltage; a current path from the source region, through the semiconductor layer, to the drain region; a sensing gate region in contact with a first surface of the semiconductor layer and having an opposite polarity as the semiconductor layer; a sensing surface in electrical communication with the sensing gate region; and a dual gate region that is in contact with a second side of the semiconductor layer located opposite to the first side of the semiconductor layer; wherein the dual gate region has a same polarity as the sensing gate region.

In another embodiment of the invention, a biosensor comprises a semiconductor region having a doping polarity; a source region located at a first end of the semiconductor layer and a drain region located at a second end of the semiconductor layer; wherein the source region is in electrical communication with a source voltage; a current path from the source region, through the semiconductor layer, to the drain region; a sensing gate region is in contact with a first surface of the semiconductor layer and having an opposite polarity as the semiconductor layer; a floating gate comprising an extended region; wherein the floating gate is located on the first surface of the semiconductor layer; wherein a first insulating layer is located in between the first surface of the semiconductor layer and the floating gate and covers the sensing gate region; a dual gate region located on the first side of the semiconductor layer; wherein the floating gate is located in between the dual gate region and the sensing gate region; wherein a second insulating region is located in between the dual gate region and the floating gate;

BRIEF DESCRIPTION OF THE DRAWINGS

Refer now to the figures, which are exemplary embodiments, and wherein the like elements are numbered alike and where

FIG. 9 is an illustration of an embodiment of a semiconductor layer;

FIG. 10 is an illustration of an embodiment of a dual gate region formed in a semiconductor layer;

FIG. 11 is an illustration of an embodiment of a semiconductor layer and a hardmask layer formed on a semiconductor layer;

FIG. 12 is an illustration of an embodiment of a shallow trench isolation formed in a biosensor;

FIG. 13 is an illustration of an embodiment of a partially recessed shallow trench isolation in a biosensor;

FIG. 14 is an illustration of an embodiment of a source region and a drain region formed in a biosensor;

FIG. 15 is an illustration of an embodiment of a passivation layer formed on the biosensor;

FIG. 16 is an illustration of an embodiment of a sensing gate region formed on the biosensor.

DETAILED DESCRIPTION

Biosensors based on electrochemical processes can be used to detect a chemical change (such as a change in pH) or the presence of a biological substance (such as enzymes, antibodies, and DNA and miRNA) by using a transducing element to convert a detection event into an electrical signal.

Figure 1:
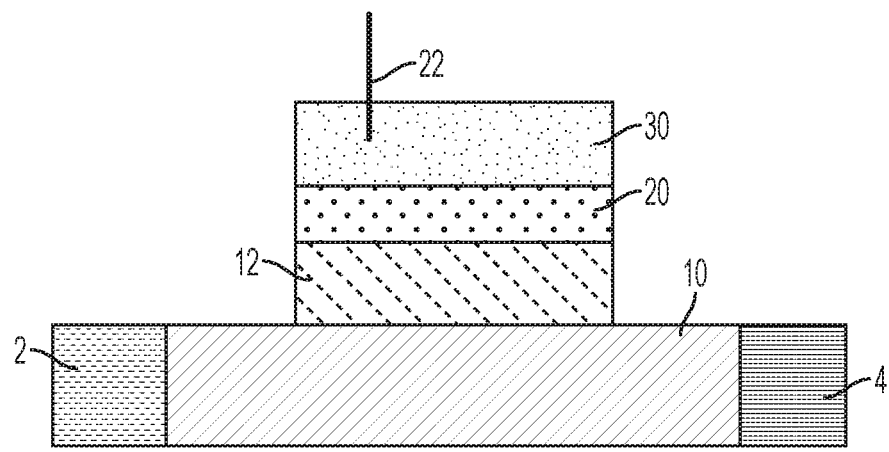
FIG. 1 is a cross-sectional illustration of an embodiment of a single gate junction field effect transistor (JFET) sensor having a reference electrode.

An example of a junction field effect transistor is illustrated in FIG. 1. A junction field effect transistor can comprise a high resistivity semiconductor material (such as silicon), illustrated as semiconductor region 10. The semiconductor material can form either an n-type or a p-type channel with an ohmic electrical connection at opposing ends of the channel, referred to herein as the source region 2 and the drain region 4. The semiconductor material can further comprise a third electrical connection, referred to as the sensing gate region 12. The sensing gate region can have an opposite doping polarity as the channel, thereby forming a p-n-junction. A sensing surface 20 can be located on the sensing gate region 12. A current flowing between the source region and the drain region can be the sensing signal. The current is a function of the strength of the electric field generated at the sensing gate region that is in contact with a sensing surface in contact with a sensing solution. Here, the current changes based on the chemical properties of the sensing solution being probed. Reference electrode 22 is present in the sensing solution for applying a voltage to the liquid sensing solution. The reference electrode 22 voltage is used to set the quiescent operation point of the sensor.

In contrast to the biosensor of FIG. 1, the present junction field effect transistor biosensor is a dual gate biosensor, which has the added benefit in that the dual gate biosensor can be used without a reference electrode. The dual gate biosensor comprises a sensing gate region that is in contact with a sensing surface and a dual gate region that can be used for adjusting the quiescent operation point of the sensor. Elimination of the reference electrode is advantageous as the functionality of the biosensor, for example, for wearable electronics, becomes simplified and the miniaturization of the biosensor is facilitated. Also, when the biosensor does not rely on a reference electrode, then the biosensor can be used, not only for detecting an analyte present in a liquid mixture, but the biosensor can be used to detect an analyte in air. The dual gate biosensor has the added benefit of one or more of a high sensitivity, a long-term reliability, and a low noise.

Figure 2:
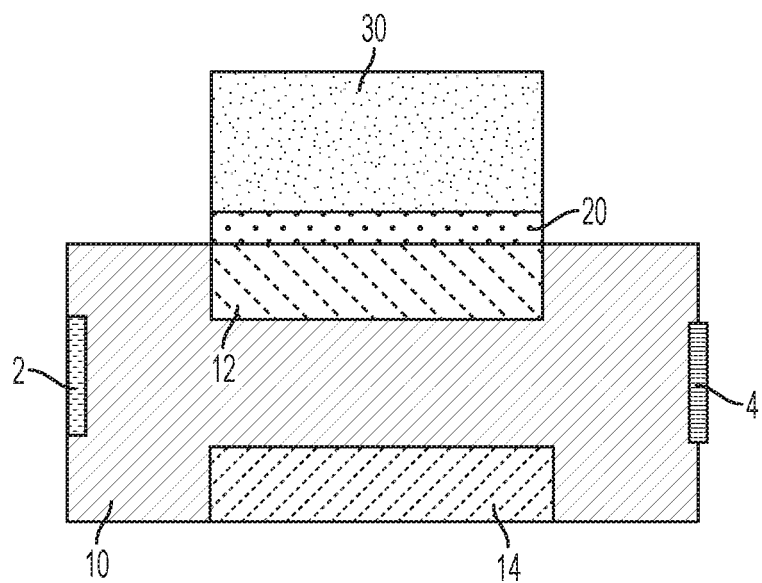
FIG. 2 is a cross-sectional illustration of an embodiment of a dual gate biosensor.

FIG. 2 is a cross-sectional illustration of a dual gate biosensor. The biosensor comprises semiconductor region 10 having a doping polarity that is n-type or p-type. When the semiconductor region 10 has an n-type doping polarity, then the semiconductor region 10 can be doped with a donor impurity (such as phosphorus) that allows for the flow of the current though the semiconductor region 10 to be a negative flow in the form of electrons. Here, the voltage applied to the source region can be 0 volts, the voltage applied to the drain region can be greater than 0 volts, and the voltage applied to the dual gate region can be less than 0 volts.

When the semiconductor region 10 has a p-type doping polarity, then the semiconductor region 10 can be doped with an acceptor impurity (such as boron) that allows for the flow of the current though the semiconductor region 10 to be a positive flow in the form of holes. Here, the voltage applied to the source region can be 0 volts, the voltage applied to the drain region can be less than 0 volts, and the voltage applied to the dual gate region can be greater than 0 volts. In situations where the voltage applied to the source is not 0 volts, then the voltage applied to the drain can be more negative than the voltage applied to the source, and the voltage applied to the dual gate can be more positive than the voltage applied to the source.

For the dual gate biosensor, the sensing signal can be the drain current.

Source region 2 can be located at a first end of the semiconductor layer and drain region 4 can be located at a second end of the semiconductor layer. Source region 2 can be in electrical communication with a source voltage; and the biosensor can comprise a current path from the source region, through the semiconductor layer, to the drain region.

Semiconductor region 10, source region 2, and drain region 4 can each independently have a thickness of 5 to 80 nanometers, specifically, 20 to 60 nanometers. Yet, in another aspect, the semiconductor layer can have a thickness about or in any range of 5, 10, 15, 20, 25, 30, 35, 40, 45, 50, 55, 60, 65, 70, 75, and 80 nm.

The biosensor further comprises sensing gate region 12 and dual gate region 14. Sensing gate region 12 can be in contact with a first surface of semiconductor region 10 and has an opposite polarity as semiconductor region 10. Dual gate region 14 can be in contact with a second surface of semiconductor region 10 located opposite to the first surface of semiconductor layer 10. Here, sensing surface 20 is located on top of sensing gate region 12 and is in contact with sensing mixture 30. Sensing gate region 12 and dual gate region 14 can comprise an n-type semiconductor or a p-type semiconductor. If semiconductor region 10 is p-type, then sensing gate region 12 and dual gate region 14 are n-type. Conversely, if semiconductor region 10 is n-type, then sensing gate region 12 and dual gate region 14 are p-type.

Figure 3:
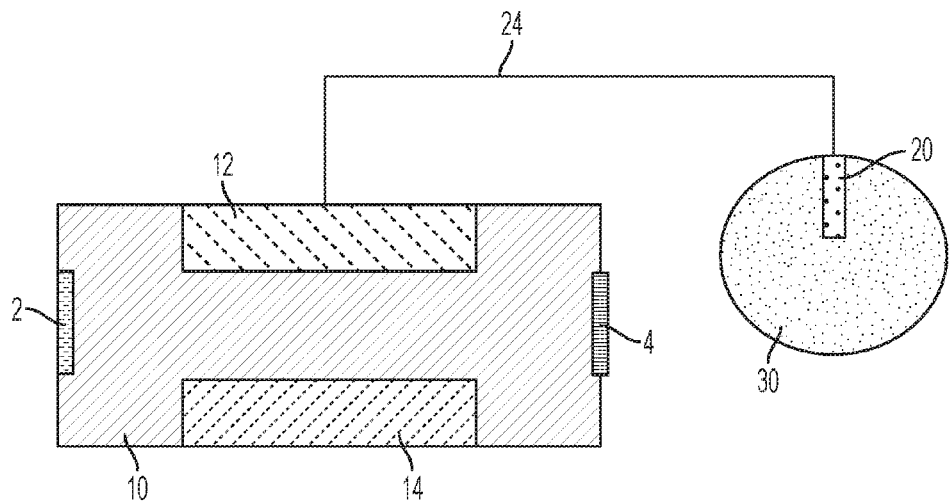
FIG. 3 is a cross-sectional illustration of an embodiment of a dual gate biosensor comprising a remote sensing surface.

FIG. 2 illustrates that sensing surface 20 can be located on sensing gate region 12, whereas FIG. 3 illustrates that sensing surface 20 can be a remote sensing surface connected to sensing gate region 12 by lead 24. Sensing surface 20 can be in contact with sensing mixture 30 that can comprise a liquid. Due to the dual gate biosensor being free of a reference electrode, sensing surface 20 can be in contact with sensing mixture 30 that can comprise a gas.

Sensing surface 20 can detect the presence of an ion (such as a chloride ion), a protein, a gas (such as a reducible gas), a sulfur containing compound, or a combination comprising at least one of the foregoing. Sensing surface 20 can be functionalized to detect the presence of a biological molecule such as a protein. Sensing surface 20 can be functionalized to detect the presence of a biological molecule such as one or more of an enzyme, an antigen, a hormone, a bacteria, a virus, or a combination comprising at least one of the foregoing.

Sensing surface 20 can comprise a metal, for example, titanium nitride (TiN) for measuring pH; Ag/AgCl for detecting chloride ions; or gold for detecting proteins, DNA, miRNA using thiol chemistry based surface functionalization. Sensing surface 20 can comprise a dielectric layer, such as silicon dioxide ($SiO_2$), hafnium oxide ($HfO_2$), titanium dioxide ($TiO_2$), or a combination comprising at least one of the foregoing.

Figure 4:
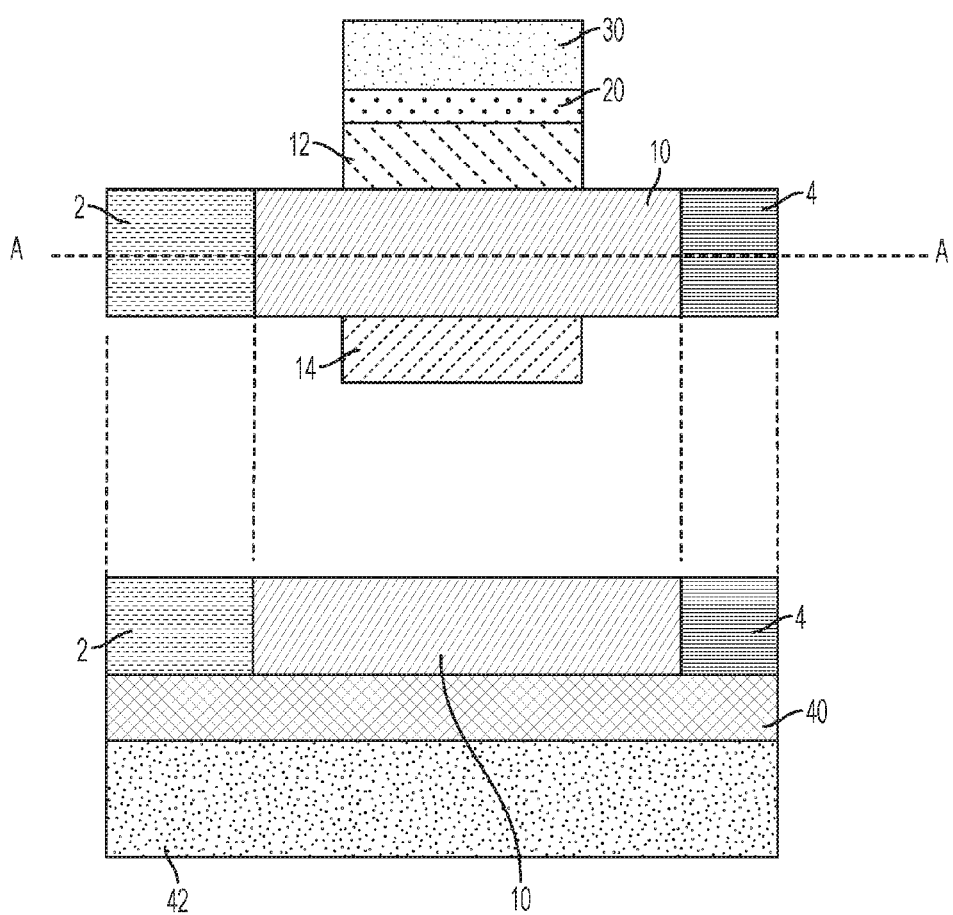
FIG. 4 is a cross-sectional illustration of an embodiment of a dual gate biosensor on a semiconductor-on-insulator wafer.

FIG. 4 illustrates that the biosensor can be located on a semiconductor-on-insulator (SOI) substrate, such as a silicon-on-insulator substrate. Here, semiconductor layer 10 can be located on semiconductor layer 42 (such as a silicon wafer), where buried oxide (BOX) layer 40 can be located in between semiconductor layer 10 and semiconductor layer 42. FIG. 4 further illustrates in the below image, a cross-sectional illustration taken along line A to illustrate semiconductor layer 10 being located on the semiconductor-on-insulator substrate.

Semiconductor layer 42 can comprise Si (silicon), strained Si, SiC (silicon carbide), Ge (germanium), SiGe (silicon germanium), SiGeC (silicon-germanium-carbon), Si alloys, Ge alloys, GaAs (gallium arsenide), InAs (indium arsenide), InP (indium phosphide), cadmium arsenide, cadmium selenide, or a combination comprising at least one of the foregoing. Buried oxide layer can comprise an oxide, for example, silicon dioxide, and/or a nitride, for example, silicon nitride.

Semiconductor layer 42 can have a thickness of 0.1 to 750 micrometers. The substrate can comprise bulk Si and can have a thickness of 700 to 800 micrometers. The semiconductor layer 10 can have a thickness of 5 to 100 nanometers.

FIG. 4 illustrates that sensing gate region 12 can be located on one side of semiconductor layer 10, and dual gate region 14 on one side of semiconductor layer 10 opposite sensing gate region 12. FIG. 4 further illustrates that sensing surface 20 can be located on sensing gate region 12 and in contact with sensing mixture 30.

Figure 5:
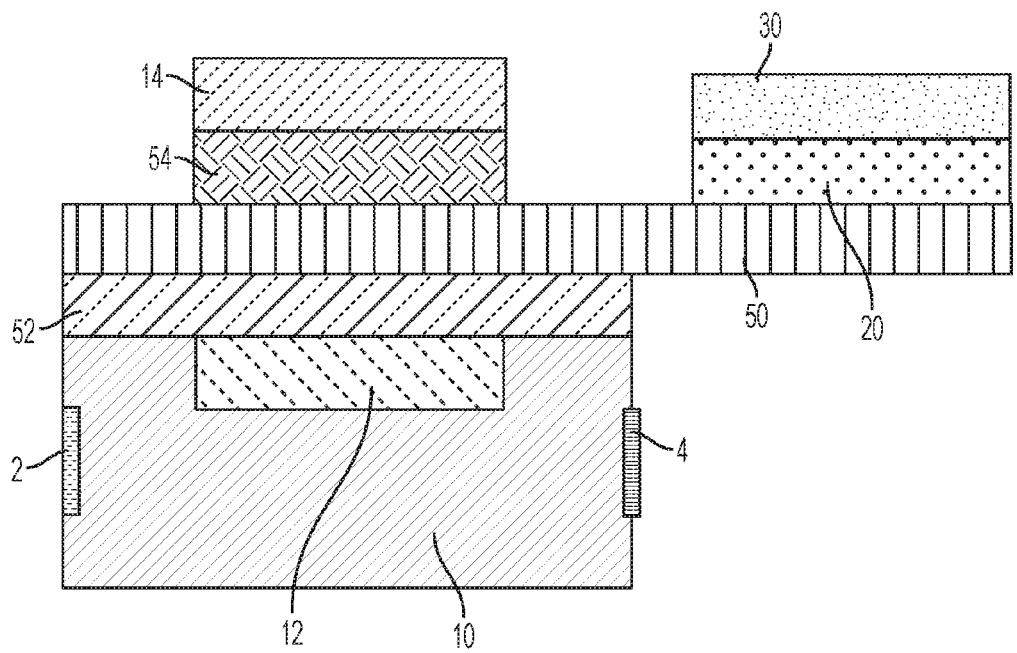
FIG. 5 is a cross-sectional illustration of an embodiment of a dual gate biosensor comprising a floating gate.

FIG. 5 illustrates that the biosensor can comprise a floating gate. Here, the biosensor comprises source region 2, semiconductor region 10, drain region 4, sensing gate region 12, and dual gate region 14, and further comprises floating gate 50. Floating gate 50 can be located in between first insulating layer 52 and second insulating layer 54. First insulating layer 52 can be located in between sensing gate region 12 and floating gate 50. Second insulating layer 54 can be located in between floating gate 50 and dual gate region 14. First insulating layer 52 and second insulating layer 54 can each independently comprise an oxide (such as silicon dioxide, hafnium oxide, high aspect ratio plasma (HARP) oxide, high temperature oxide (HTO), tetraethylorthosilicate (TEOS) oxide, and high density plasma (HDP) oxide), a nitride (such as silicon oxynitride), or a combination comprising at least one of the foregoing.

FIG. 5 illustrates that sensing surface 20 can be located on an extended portion of floating gate 50 and can be in contact with sensing mixture 30. Due to the presence of dual gate region 14, the biosensor of FIG. 5 can be free of the reference electrode.

FIGS. 9-17 illustrate an embodiment of a method of forming the dual gate biosensor.

Figure 9:
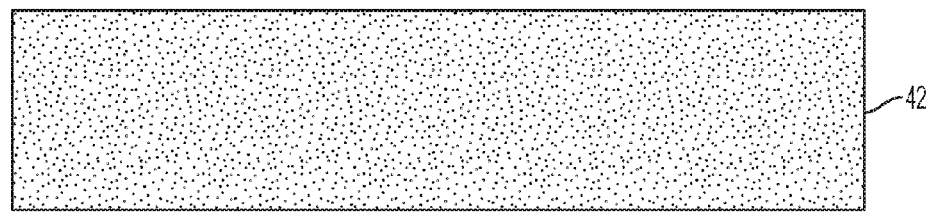
FIGS. 9-16 illustrate an embodiment of a method of preparing a biosensor.

FIG. 9 illustrates starting with semiconductor layer 42. Semiconductor layer 42 can comprise silicon. Semiconductor layer 42 can be p-type or n-type.

Figure 10:
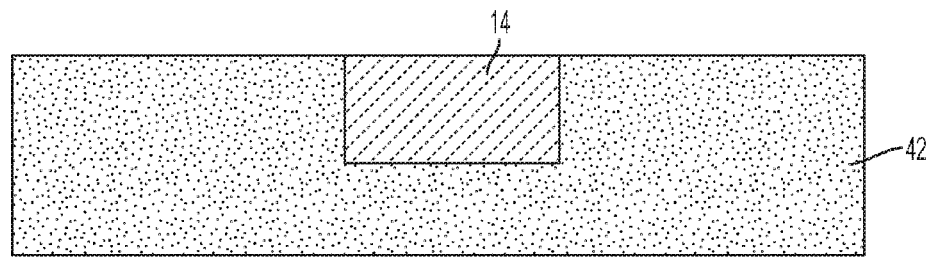

FIG. 10 illustrates that dual gate region 14 can be formed in semiconductor layer 42. Dual gate region 14 can be formed by heavily doping the region with a p-type dopant for a p-type gate or with n-type dopants for an n-type gate.

Figure 11:
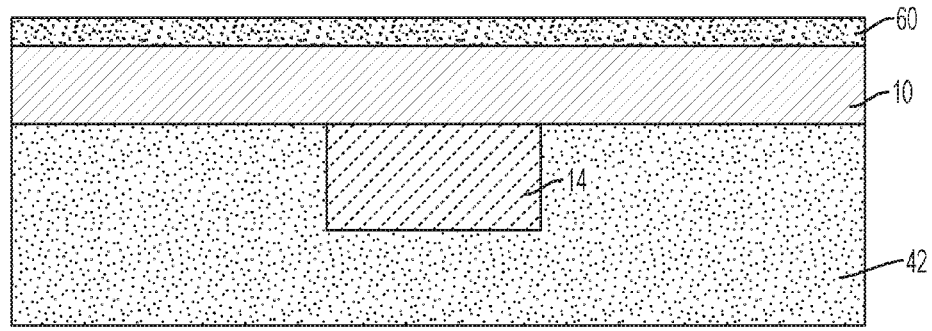

FIG. 11 illustrates that semiconductor layer 10 can be formed on semiconductor layer 42 and that hardmask layer 60 can be deposited on semiconductor layer 10. A semiconductor growth process (for example, and epitaxial growth process) can be used to form semiconductor layer 10. The semiconductor growth process can be performed to grow a crystalline layer of silicon germanium, for example, onto the crystalline semiconductor layer 42 beneath, where the underlying semiconductor can act as a seed crystal. Semiconductor layer 10 can be grown from gaseous or liquid precursors. A non-limiting example of a suitable material (element) for semiconductor layer 10 includes silicon germanium. The silicon germanium can have a germanium content of 40 to 70 atomic % (at. %).

Semiconductor layer 10 can be grown using a suitable growth process, for example, chemical vapor deposition (CVD), liquid phase (LP) chemical vapor deposition, reduced pressure chemical vapor deposition (RPCVD), vapor-phase epitaxy (VPE), molecular-beam epitaxy (MBE), liquid-phase epitaxy (LPE), metal organic chemical vapor deposition (MOCVD), or other suitable processes.

Dual gate region 14 can comprise an n-type semiconductor or a p-type semiconductor. If dual gate region 14 is n-type, then semiconductor layer 10 can be p-type; and, conversely, if dual gate region 14 is p-type, then semiconductor layer 10 can be n-type.

Hardmask layer 60 can prevent oxidation of semiconductor layer 10, for example, during a thermal mixing process by forming a capping layer. Hardmask layer 60 can also maintain the shape of the surface of semiconductor layer 10 by preventing surface rearrangement during thermal mixing annealing. Hardmask layer can be thick enough to prevent oxygen from penetrating through to semiconductor layer 10.

Hardmask layer 60 can comprise include a dielectric material, for example, an oxide, an oxide precursor, or a nitride. Non-limiting examples of materials for forming hardmask layer 60 include silicon dioxide, silicon nitride, tetraethylorthosilicate (TEOS) oxide, high aspect ratio plasma (HARP) oxide, high temperature oxide (HTO), high density plasma (HDP) oxide, or any combination thereof. Hardmask layer 60 can be formed using a deposition process, including, but not limited to chemical vapor deposition (CVD), physical vapor deposition (PVD), plasma enhanced CVD (PECVD), atomic layer deposition (ALD), evaporation, chemical solution deposition, and/or other like processes.

Figure 12:
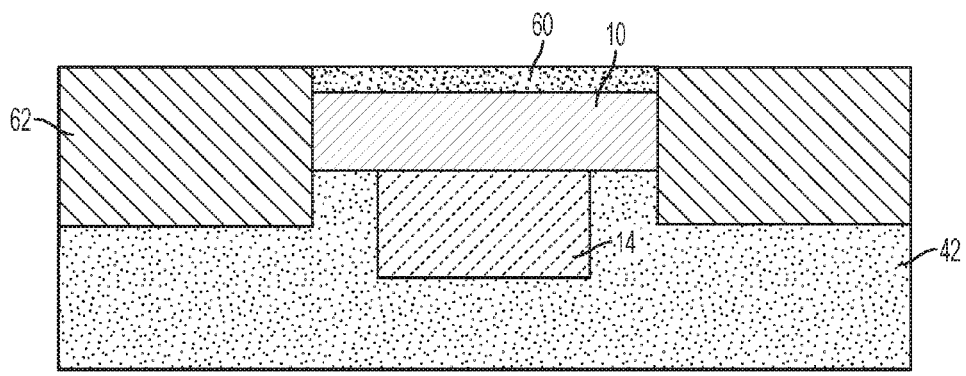

FIG. 12 illustrates that shallow trench isolation (STI) regions 62 can be formed. The shallow trench isolation (STI) regions 62 can be formed in hardmask layer 60, in semiconductor layer 10, and optionally in semiconductor layer 42. Shallow trench isolation regions 62 are isolation regions that can be formed by etching trenches in the biosensor and then filling the trenches with, for example, silicon dioxide. Other suitable oxide materials can be deposited to form the STI regions 62. Non-limiting examples of suitable oxide materials for shallow trench isolation regions 62 include silicon dioxide, tetraethylorthosilicate (TEOS) oxide, high aspect ratio plasma (HARP) oxide, silicon oxide, high temperature oxide (HTO), high density plasma (HDP) oxide, oxides formed by an atomic layer deposition (ALD) process, or a combination comprising at least one of the foregoing.

Figure 13:
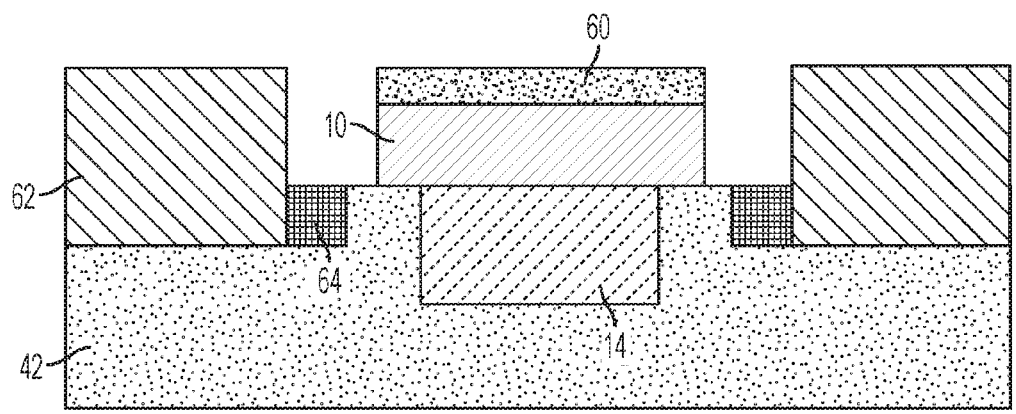
Figure 14:
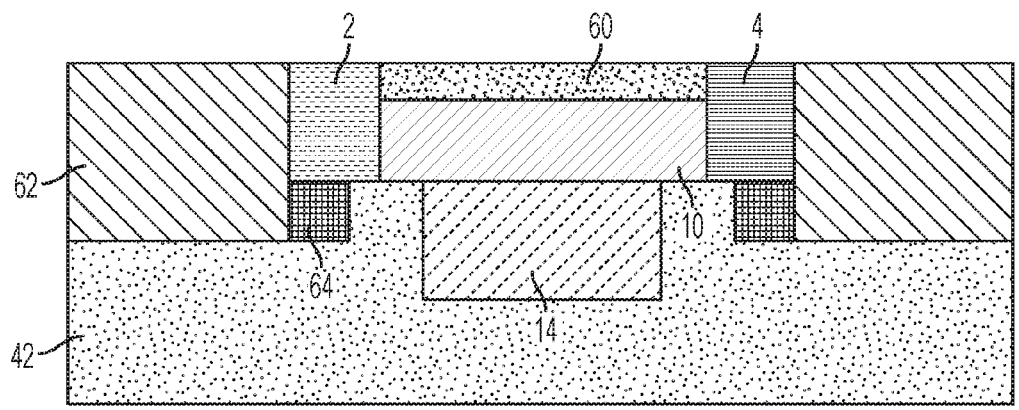

FIGS. 13 and 14 illustrate that shallow trench isolation regions 62 can be partially recessed to allow for the formation of source region 2 and drain region 4. A photoresist etch mask pattern (not shown) can be formed to allow the oxide materials filling the shallow trench isolation region 62 to be selectively removed partially in the unmasked region, as illustrated in FIG. 13. A mixture of $CF_4$ and $H_2$ can be used to etch silicon oxide selectively. Oxide regions 64 illustrate the remaining oxide materials after the shallow trench isolation 62 is partially recessed. Regions 64 serve the purpose of reducing the interface area between source region 2 and substrate 42, and reducing the interface area between drain region 4 and substrate 42. The result is reduced capacitance associated with source 2 and drain 4. Capacitance reduction regions 64 can be formed prior to formation of source region 2 and drain region 4. Capacitance reduction regions 64 can comprise an oxide.

Source region 2 and drain region 4 can be formed by depositing an n-type polysilicon or a p-type polysilicon in the recessed region followed by polishing, for example, by chemical and mechanical polishing to planarize the surface of the biosensor.

Figure 15:
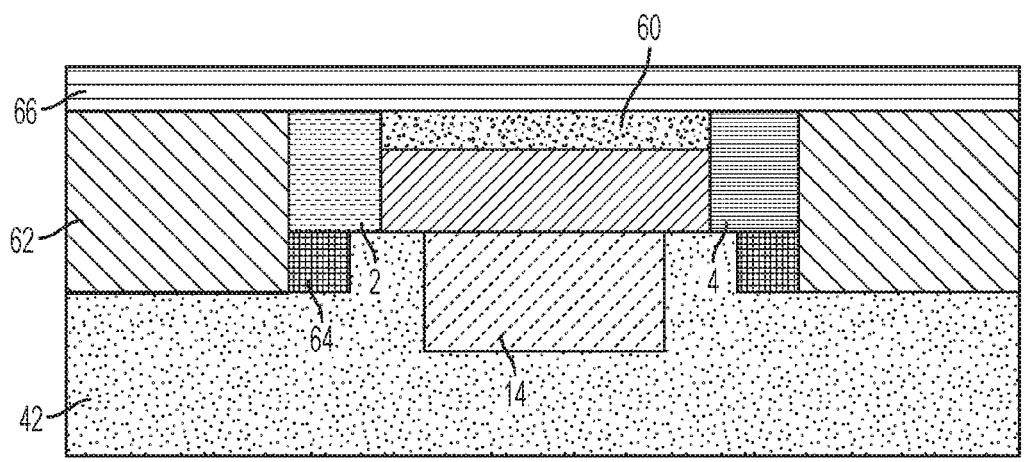
Figure 16:
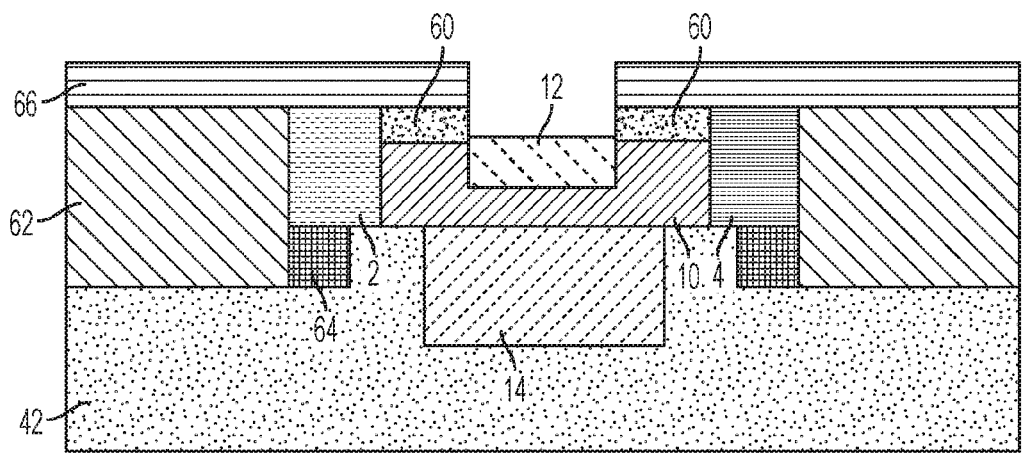
Figure 17:
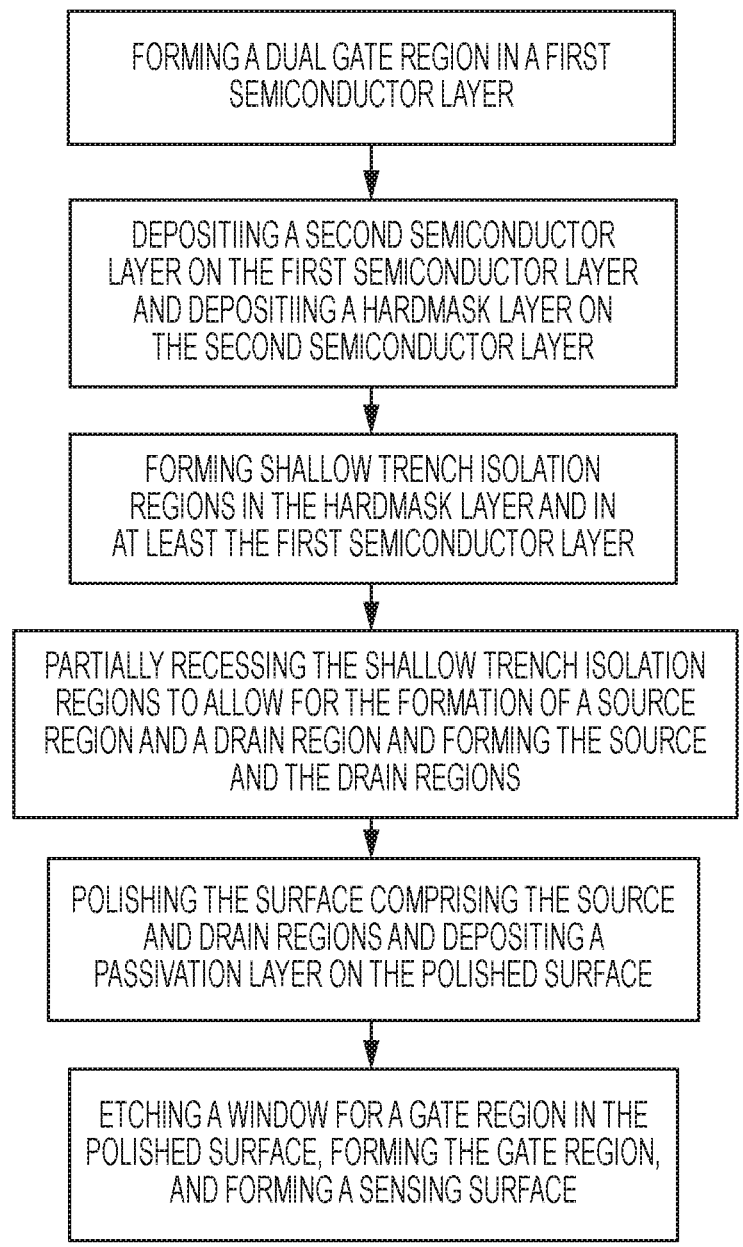
FIG. 17 is an illustration of an embodiment of forming the biosensor.

FIGS. 15 and 16 illustrate that passivation layer 66 can be deposited on the polished surface of the biosensor followed by etching to open a window for a gate region, where sensing gate region 12 can be formed. A sensing surface (not illustrated) can then be formed on sensing gate region 12 or a lead 24 can be connected to sensing gate region 12 and the sensing surface.

Etching to open a window of the gate region can comprise forming an unmasked region in a mask layer (such as photoresists, electron-beam resists, ion-beam resists, X-ray resists, and etchant resists) and etching the passivation layer 66 and the hardmask layer 60 (for example, by reactive ion etching (ME), a remote plasma, diluted HF, or chemical vapor/sublimation). Non-limiting examples of suitable etching processes include oxide etching methods selective to silicon. As used herein, the reactive ion etching can comprise a simultaneous exposure to hydrogen (H$_2$), nitrogen trifluoride (NF$_3$), and ammonia (NH$_3$) plasma by-products (SiCoNi process). Any remaining mask layer can be removed, for example, using a solvent or an aqueous developer, for example, using N-methyl-2-pyrrolidone (NMP), toluene, propylene glycol methyl ether acetate (PGMEA), tetramethylammonium hydroxide (TMAH), or a combination comprising at least one of the foregoing.

FIG. 16 illustrates the sensor structure after sensing gate region 12 has been formed. Sensing gate region 12 can be formed by doping the semiconductor layer 10 region exposed by the gate region window. Ion implantation of dopants can be employed to form the sensing gate region 12. When a sensing mixture is introduced to the sensing surface, that source region 2 and drain region 4 can be isolated from the sensing mixture, for example, owning at least to the presence of passivation layer 66.

The biosensor can be used to probe a biological fluid such as sweat or saliva. The biosensor can be used to probe sweat, for example, by adhesively applying (for example, using a tape) the biosensor to the wearer or by mechanically attaching (for example, using a wrist band) the biosensor to the wearer. The biosensor can be used to probe saliva, for example, by mounting the biosensor to a mouth guard.

When the biosensor is a dual gate biosensor and when the reference electrode is not present, then the biosensor can advantageously be used to probe surfaces that are dry or are not continuously wet. For example, the biosensor can be used to probe air or the surface of a wearer's skin.

EXAMPLES

An n-type biosensor according to FIG. 1 using a titanium nitride sensing surface was prepared and used to probe the pH of a solution. The results are shown in FIGS. 6-8.

Figure 6:
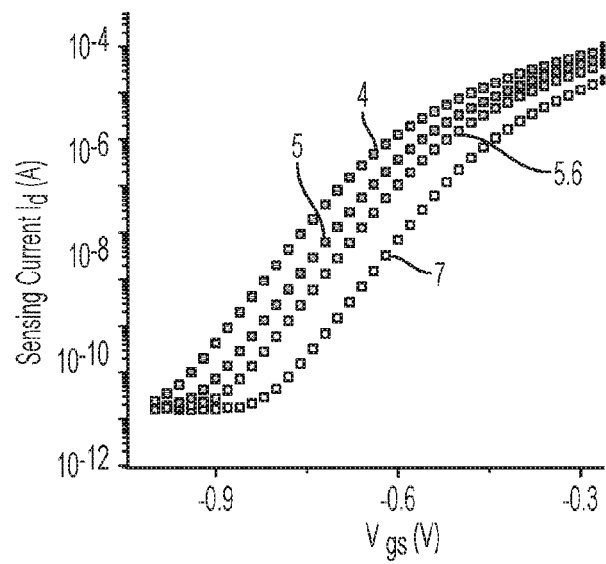
FIG. 6 is a graphical illustration of the sensing current as a function of gate voltage as measured in solutions of varying pH.

FIG. 6 is a graphical illustration of the sensing current, I$_d$, in amps (A) as a function of gate voltage, V$_{gs}$, in volts (V) as measured in solutions of varying pH. FIG. 6 shows that the subthreshold slope is 59 millivolts per decade (mV/dec).

Figure 7:
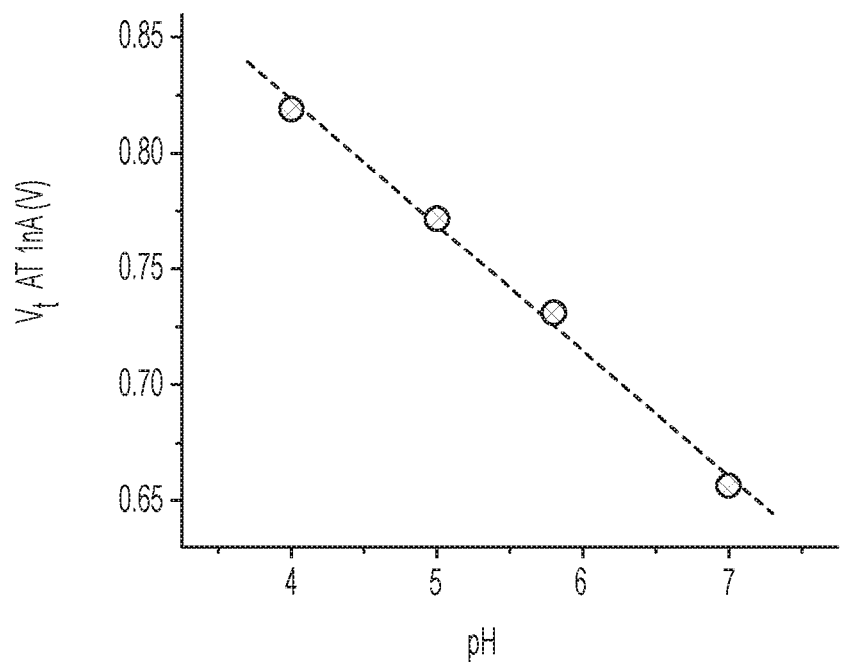
FIG. 7 is a graphical illustration of voltage as a function of pH at 1 nanoamp.

FIG. 7 is a graphical illustration of the threshold voltage, V$_t$, in volts (V) at 1 nanoamp (nA) as a function of pH. FIG. 7 shows that the sensitivity is 55 millivolts per pH.

Figure 8:
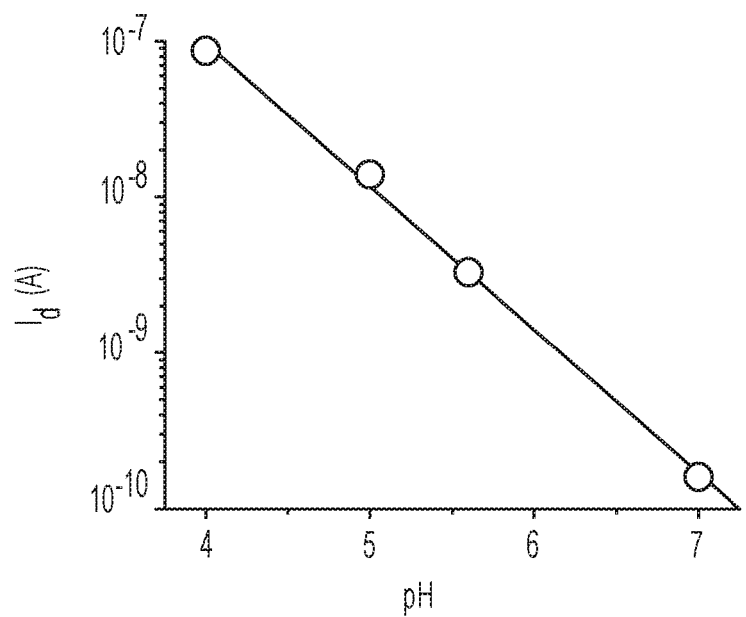
FIG. 8 is a graphical illustration of the current as a function of pH at a gate voltage of −0.7 volts.

FIG. 8 is a graphical illustration of the current, I$_d$, in amps (A) as a function of pH at a gate voltage of −0.7 volts. FIG. 8 shows that there is a 9.4 times change in the current per pH.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the disclosure and the practical application, and to enable others of ordinary skill in the art to understand the invention for various embodiments with various modifications as are suited to the particular use contemplated.

The diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of this disclosure.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It will also be understood that when an element, such as a layer, region, or substrate is referred to as being "on" or "over" another element, it can be directly on the other element or intervening elements may also be present. In contrast, when an element is referred to as being "directly on" or "directly over" another element, there are no intervening elements present.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A biosensor comprising:
   a semiconductor region having a doping polarity;
   a source region located at a first end of the semiconductor region and a drain region located at a second end of the semiconductor region, wherein the source region is in electrical communication with a source voltage;
   a current path from the source region, through the semiconductor region, to the drain region;
   a sensing gate region in contact with a first surface of the semiconductor region and having an opposite polarity as the semiconductor region;
   a sensing surface in electrical communication with the sensing gate region;
   a dual gate region that is in contact with a second surface of the semiconductor region located opposite to the first surface of the semiconductor region, wherein the dual gate region has a same polarity as the sensing gate region;
   a first oxide region that is in contact with a first side of the source region located opposite to the first end of the semiconductor region, wherein a portion of the first oxide region extends to partially contact a second side of the source region such that an interface area between the second side of the source region and a substrate is reduced; and
   a second oxide region that is in contact with a first side of the drain region located opposite to the second end of the semiconductor region, wherein a portion of the second oxide region extends to partially contact a second side of the drain region such that an interface area between the second side of the drain region and the substrate is reduced.

2. The biosensor of claim 1, wherein the sensing surface is in electrical communication with the sensing gate region via a lead.

3. The biosensor of claim 1, wherein the sensing surface is located on the sensing gate region.

4. The biosensor of claim 1, wherein the biosensor further comprises a semiconductor layer and a buried oxide layer; wherein the semiconductor layer is in contact with the second surface of the semiconductor region and wherein the buried oxide layer is located in between the semiconductor region and the semiconductor layer.

5. The biosensor of claim 4, wherein the semiconductor layer comprises silicon, strained silicon, silicon carbide, germanium, silicon germanium, silicon-germanium-carbon, a silicon alloy, a germanium alloy, gallium arsenide, indium arsenide, indium phosphide, cadmium arsenide, cadmium selenide, or a combination comprising at least one of the foregoing.

6. The biosensor of claim 1, wherein the sensing surface comprises titanium nitride, gold, silicon dioxide, silver, hafnium, oxide, titanium dioxide, or a combination comprising at least one of the foregoing.

7. The biosensor of claim 1, wherein the sensing surface comprises a functionalization.

8. The biosensor of claim 1, wherein the semiconductor region has an n-type polarity and wherein the sensing gate region and the dual gate region have a p-type polarity.

9. The biosensor of claim 1, wherein the semiconductor region, the source region, and the drain region each independently have a thickness of 5 to 80 nanometers.

10. A biosensor comprising:
a semiconductor region having a doping polarity;
a source region located at a first end of the semiconductor region and a drain region located at a second end of the semiconductor region, wherein the source region is in electrical communication with a source voltage;
a current path from the source region, through the semiconductor region, to the drain region;
a sensing gate region is in contact with a first surface of the semiconductor region and having an opposite polarity as the semiconductor region;
a floating gate comprising an extended region, wherein the floating gate is located on the first surface of the semiconductor region, wherein a first insulating layer is located in between the first surface of the semiconductor region and the floating gate and covers the sensing gate region;
a dual gate region located on the first surface of the semiconductor region, wherein the floating gate is located in between the dual gate region and the sensing gate region, wherein a second insulating region is located in between the dual gate region and the floating gate, and wherein the dual gate region is an electrically conducting region;
a sensing surface in electrical communication with the sensing gate region, wherein the sensing surface is located on the extended region of the floating gate;
a first oxide region, that is in contact with a first side of the source region located opposite to the first end of the semiconductor region, wherein a portion of the first oxide region extends to partially contact a second side of the source region such that an interface area between the second side of the source region and a substrate is reduced: and a second oxide region, that is in contact with a first side of the drain region located opposite to the second end of the semiconductor region, wherein a portion of the second oxide region extends to partially contact a second side of the drain region such that an interface area between the second side of the drain region and the substrate is reduced.

11. The biosensor of claim 10, wherein the biosensor further comprises a substrate and a buried oxide layer; wherein the substrate is in contact with a second surface of the semiconductor region and wherein the buried oxide layer is located in between the semiconductor region and the substrate.

12. The biosensor of claim 10, wherein the sensing surface comprises titanium nitride, gold, silver, silicon dioxide, hafnium, oxide, titanium dioxide, or a combination comprising at least one of the foregoing.

13. The biosensor of claim 10, wherein the sensing surface comprises a functionalization.

14. The biosensor of claim 10, wherein the first insulating layer and the second insulating layer each independently comprise an oxide, a nitride, or a combination comprising at least one of the foregoing.

15. The biosensor of claim 10, wherein the semiconductor region, the source region, and the drain region each independently have a thickness of 5 to 80 nanometers.

16. A method of probing a mixture using a biosensor, the method comprising:
exposing a sensing surface to the mixture;
wherein the biosensor comprises
a semiconductor region having a doping polarity;
a source region located at a first end of the semiconductor region and a drain region located at a second end of the semiconductor region, wherein the source region is in electrical communication with a source voltage;
a current path from the source region, through the semiconductor region, to the drain region;
a sensing gate region is in contact with a first surface of the semiconductor region and having an opposite polarity as the semiconductor region;
the sensing surface in electrical communication with the sensing gate region;
a dual gate region that is contact with a second surface of the semiconductor region located opposite to the first surface of the semiconductor region, wherein the dual gate region has a same polarity as the sensing gate region;
a first oxide region that is in contact with a first side of the source region located opposite to the first end of the semiconductor region, wherein a portion of the first oxide region extends to partially contact a second side of the source region such that an interface area between the second side of the source region and a substrate is reduced; and
a second oxide region that is in contact with a first side of the drain region located opposite to the second end of the semiconductor region, wherein a portion of the second oxide region extends to partially contact a second side of the drain region such that an interface area between the second side of the drain region and the substrate is reduced.

17. The method of claim 16, wherein the mixture is a liquid.

18. The method of claim 16, wherein the probing comprising detecting the presence of an ion, a protein, a gas, a sulfur containing compound, or a combination comprising at least one of the foregoing.

19. The method of claim 16, wherein the probing comprising detecting the presence of an enzyme, an antigen, a hormone, a bacteria, a virus, or a combination comprising at least one of the foregoing.

20. The method of claim 16, wherein the mixture is a gas.

* * * * *